United States Patent [19]
Jensen

[11] Patent Number: 5,683,439
[45] Date of Patent: *Nov. 4, 1997

[54] POST-OPERATIVE THERMAL BLANKET

[75] Inventor: Marvin E. Jensen, Mundelein, Ill.

[73] Assignee: Hollister Incorporated, Libertyville, Ill.

[*] Notice: The term of this patent shall not extend beyond the expiration date of Pat. No. 5,470,353.

[21] Appl. No.: 443,344

[22] Filed: May 17, 1995

Related U.S. Application Data

[63] Continuation of Ser. No. 139,286, Oct. 20, 1993, Pat. No. 5,470,353.

[51] Int. Cl.$^6$ ............................................. A61F 7/00
[52] U.S. Cl. ........................... 607/104; 607/114; 607/108
[58] Field of Search ........................... 607/104, 108–112, 607/114; 602/1, 2, 14

[56] References Cited

U.S. PATENT DOCUMENTS

| | | | |
|---|---|---|---|
| 2,299,162 | 10/1942 | Merick . | |
| 3,178,559 | 4/1965 | Fogel et al. . | |
| 3,714,947 | 2/1973 | Hardy | 607/104 |
| 3,901,225 | 8/1975 | Sconce | 607/112 |
| 4,114,620 | 9/1978 | Moore et al. . | |
| 4,118,946 | 10/1978 | Tubin . | |
| 4,149,541 | 4/1979 | Gammons et al. . | |
| 4,172,495 | 10/1979 | Zebuhr et al. | 607/110 |
| 4,382,446 | 5/1983 | Truelock et al. . | |
| 4,575,097 | 3/1986 | Brannigan et al. | 607/112 |
| 4,765,338 | 8/1988 | Turner et al. . | |
| 4,805,620 | 2/1989 | Meistrell | 607/112 |
| 4,951,665 | 8/1990 | Schneider . | |
| 4,982,736 | 1/1991 | Schneider . | |
| 5,133,348 | 7/1992 | Mayn . | |
| 5,174,285 | 12/1992 | Fontenot | 607/104 |
| 5,190,032 | 3/1993 | Zacol | 607/109 |
| 5,230,335 | 7/1993 | Johnson, Jr. et al. | 607/108 |
| 5,241,951 | 9/1993 | Mason et al. | 607/104 |
| 5,336,255 | 8/1994 | Kanare et al. | 607/112 X |

*Primary Examiner*—Jennifer Bahr
*Assistant Examiner*—Ryan Carter
*Attorney, Agent, or Firm*—Tilton Fallon Lungmus

[57] ABSTRACT

A thermal blanket particularly suitable for post-operative treatment of body joints such as the shoulder, ankle, knee and elbow. The blanket includes a bodyside first panel composed of double layers of thermoplastic sheet material heat-sealed together to define at least one and preferably two serpentine fluid flow passages for the circulation of cooling (or warming) fluid. The blanket also includes a soft, foldable exterior second panel coplanar with the first panel, the edges of the two panels being secured together to form a unitary, easily-foldable blanket. The exterior panel is of soft loop-providing pile fabric over substantially the entire exterior surface thereof. The developed outline of the blanket provides it with a form defining two main sections, one of which is provided with an attachment patch (preferably elastic) having a bodyside-facing hook-providing fabric for releasable attachment to the loop-providing pile fabric of the exterior panel of the other main section when the blanket is wrapped about a joint area for administering thermal treatment. The blanket also includes an integral T-shaped section having a strap portion and an elongated limb-wrapping band portion. Flexible inlet and outlet tubes extend through the strap portion and terminate in a fluid coupling element adjacent and external to the band portion. When formed as a shoulder blanket, a pair of flaps are also provided, one serving as a chest flap and the other as a back flap with the two flaps being joined by a body strap extending about the wearer's body beneath the opposite shoulder. The body strap is equipped at its ends with hook-providing fabric patches for adjustably and releasably attaching the ends of the body strap to the pile fabric extending over the flap portions of the blanket.

3 Claims, 4 Drawing Sheets

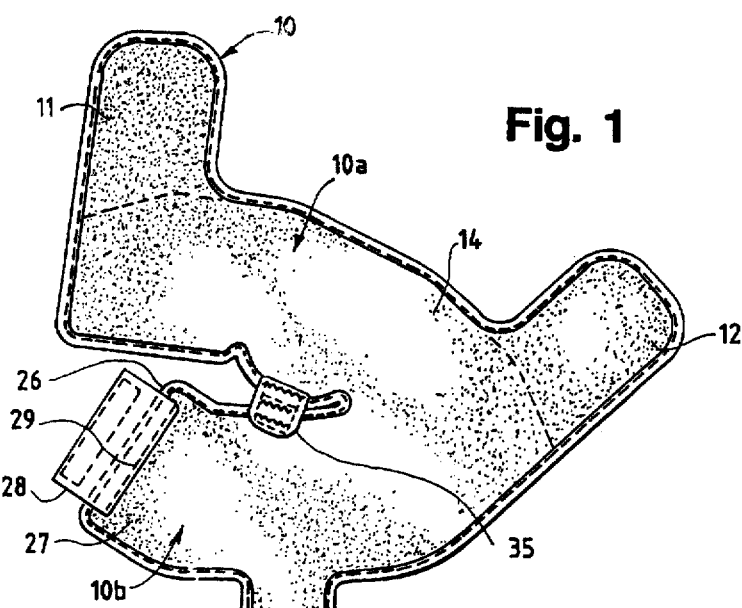
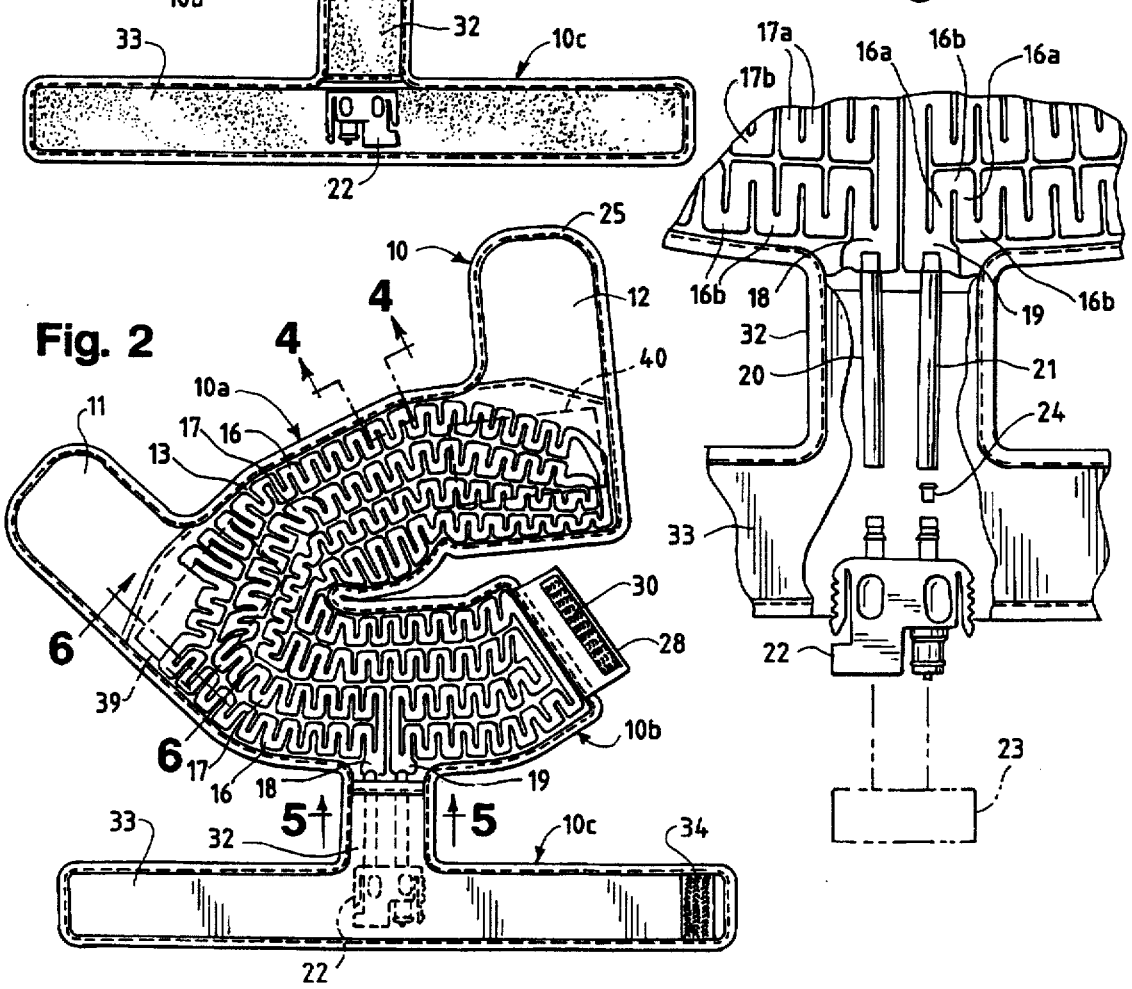

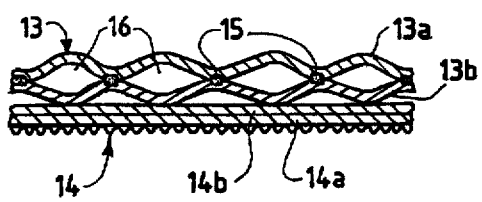
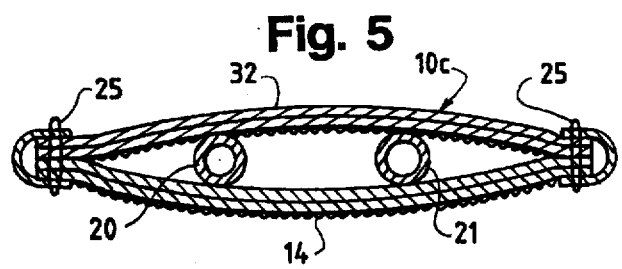
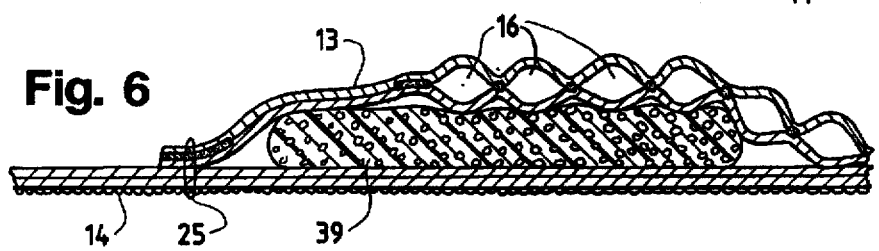
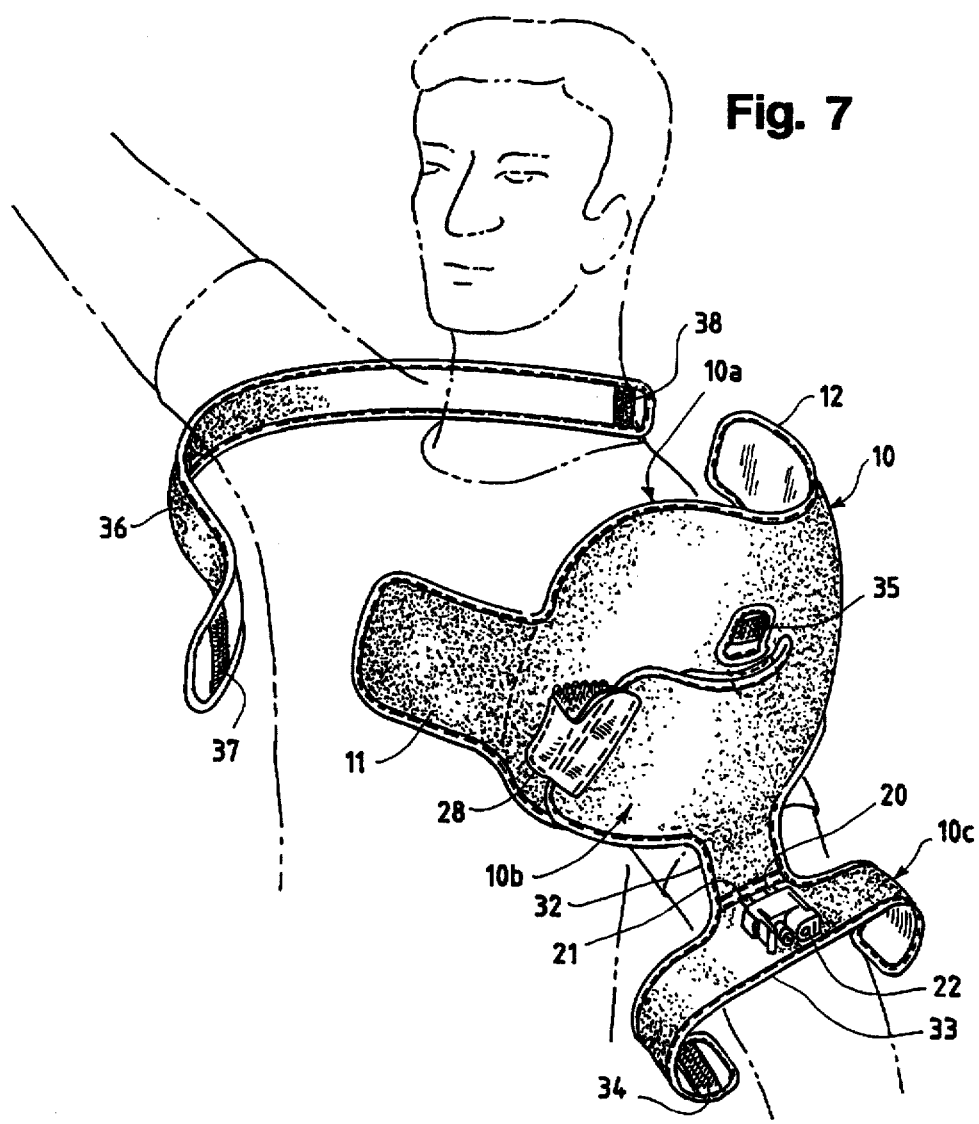

POST-OPERATIVE THERMAL BLANKET

This is a continuation of application Ser. No. 08/139,286, filed on Oct. 20, 1993.

BACKGROUND AND SUMMARY

The therapeutic use of thermal blankets having walls of flexible polymeric material that are sealed together to define a labyrinth of passages for the circulation of heating or cooling fluid is well known. While such therapy may involve either heating or cooling portions of the body, it is the cooling mode that in recent years has received particular attention because of its effectiveness in post-operative treatment and in connection with physical therapy. In particular, cryotherapy following soft tissue trauma has been shown to reduce pain, swelling, blood loss, inflammation and hematoma formation. During the rehabilitative process, cryotherapy has been utilized effectively to diminish inflammation and patient discomfort.

For such therapy, the thermal blanket should fit snugly about and uniformly contact the area of the body requiring treatment. Where the treatment site is relatively flat, or is of regular contour, these objectives may be accomplished with a blanket that normally lies flat and can be placed against, or wrapped about, the body part. However, such objectives are far more difficult to achieve when the body portion to receive thermal treatment is a joint area of complex and variable curvatures such as the shoulder, elbow, ankle or knee. In such a case, the inability of a flat blanket to assume double curvatures and follow complex body contours may seriously compromise the effectiveness of the intended treatment. An alternative approach, that of providing a pre-formed non-planar blanket sized and shaped to match the contour of the treatment site, is considered impractical for a number of reasons including manufacturing complexities and cost.

The problems of providing effective cryotherapy (or heat therapy) to a joint area using a blanket having fluid circulation passages are further complicated by the difficulties of insuring proper flow throughout the blanket when it has been folded or wrapped about the treatment site. If, for example, the blanket is of a type that allows thermal fluid to flow at random because the thermoplastic layers are joined together at a multiplicity of points that do not provide clearly-defined flow routes, then, when such a blanket is wrapped or folded about the treatment site, the thermal fluid can be expected to take the paths of least resistance and certain areas of the blanket may receive little or no fluid circulation. On the other hand, if the blanket is of a type that has defined (i.e., tubular) flow passages, there is a risk that such passages may become kinked and obstruct fluid flow when the blanket is folded or wrapped about the treatment site.

All such blankets that provide for the circulation of thermal fluid have inlet and outlet tubes leading to and from the cooling/heating/pumping equipment that controls fluid temperature and directs flow circulation. Such tubes, and the inlet and outlet passages of the blanket with which they communicate, are vulnerable to kinking, twisting, and flow obstruction as a patient moves about or changes body position during waking hours and, in particular, during sleep, when such obstruction of the passages may go unnoticed.

Accordingly, an important aspect of this invention lies in providing a blanket that is particularly suitable for the thermal treatment of joint areas and may be easily adjusted to fit patients of different size and physical characteristics notwithstanding the fact that the blanket is manufactured (and may be marketed and stored) in substantially flat or planar condition. A zigzag arrangement of dual passages extends through the blanket in directions that eliminate or greatly reduce possibilities of partial or total flow obstruction since, by reason of such arrangement, forces imposed on the passages when the blanket is properly folded or wrapped over a treatment site tend to be in the form of twisting rather than kinking forces. Kinking of inlet and outlet tubes and the inlet/outlet passages of the blanket with which they communicate is prevented by providing the blanket with an integral limb wrap that supports the tubes and the fluid coupling element(s) connected to them and immobilizes such tubes and element(s) in relation to the patient's limb. Close fitting of the blanket to the treatment site is assured by providing the planar blanket with an outline of distinctive and developed shape, by utilizing VELCRO® hook and loop attachment means, and by providing substantially the entire outer (exterior) panel of the blanket with a soft loop-providing pile fabric which constitutes the loop component of the hook-loop attachment system.

Briefly, the blanket includes a foldable bodyside panel composed of double layers of thermoplastic sheet material heat-sealed together to define at least one, and preferably two, serpentine flow passages extending along zigzag pathways from an inlet opening to an adjacent outlet opening. The blanket also includes a soft, foldable exterior panel covering the entire bodyside panel with the peripheral edges of the two panels being secured together. As stated, the entire exterior surface of the blanket is composed of a loop-providing pile fabric and at least one of the main sections of the distinctively shaped planar blanket is provided with a hook-providing attachment patch which is releasably attachable to the loop-providing exterior panel in a manner that assures a snug fit over or about the area of treatment.

The integral limb-attaching means takes the form of a T-shaped section having a central strap portion terminating in an elongated limb-wrapping band portion. The parallel and flexible inlet and outlet tubes extend along the strap portion with each tube being connected at one end to an inlet or outlet opening of the blanket and at its opposite end to a fluid coupling element that overlies the exterior surface of the T-shaped section for easy access during a coupling/uncoupling operation while, at the same time, preventing twisting and kinking of the tubes and cushioning the limb from direct contact with the coupling element.

When the blanket is configured for thermal treatment of a shoulder joint, it has a generally C-shaped outline that defines two main sections, one of which is intended to be folded over the top of the shoulder and the other about the shoulder's side (or uppermost arm) surface. A free edge of the second section is adjustably connected to the first section in partial overlapping relation by means of the hook-providing attachment patch which, preferably, is elastically stretchable in directions towards and away from that free edge. The shoulder blanket also includes flap portions which cover portions of the back and chest of the wearer and are adjustably connected by a body strap which extends about the wearer's body below the shoulder and arm opposite from the shoulder receiving thermal treatment. Additional means in the form of resilient foam pads and closure flaps insure close conformity of the blanket with the shoulder and promote more efficient and uniform thermal exchange. Because of its distinctive configuration, the shoulder blanket is adapted to cover either the patient's right or left shoulder with the same ease of application for achieving a close fit for efficient and effective therapy.

Other features, advantages and objects will appears from the specification and drawings.

DRAWINGS

FIG. 1 is a top plan view of a shoulder blanket embodying the invention.

FIG. 2 is a plan view of the underside of the blanket.

FIG. 3 is a fragmentary view, taken partly in section and in exploded condition, showing the inlet/outlet tube arrangement and coupling element of the blanket.

FIG. 4 is an enlarged and somewhat schematic sectional view taken along line 4—4 of FIG. 2.

FIG. 5 is an enlarged and somewhat schematic sectional view taken along line 5—5 of FIG. 2.

FIG. 6 is an enlarged and somewhat schematic sectional view taken along line 6—6 of FIG. 2.

FIG. 7 is an exploded perspective view illustrating how the blanket would be fitted upon a patient's left shoulder.

DETAILED DESCRIPTION OF PREFERRED EMBODIMENT

Figure 8:
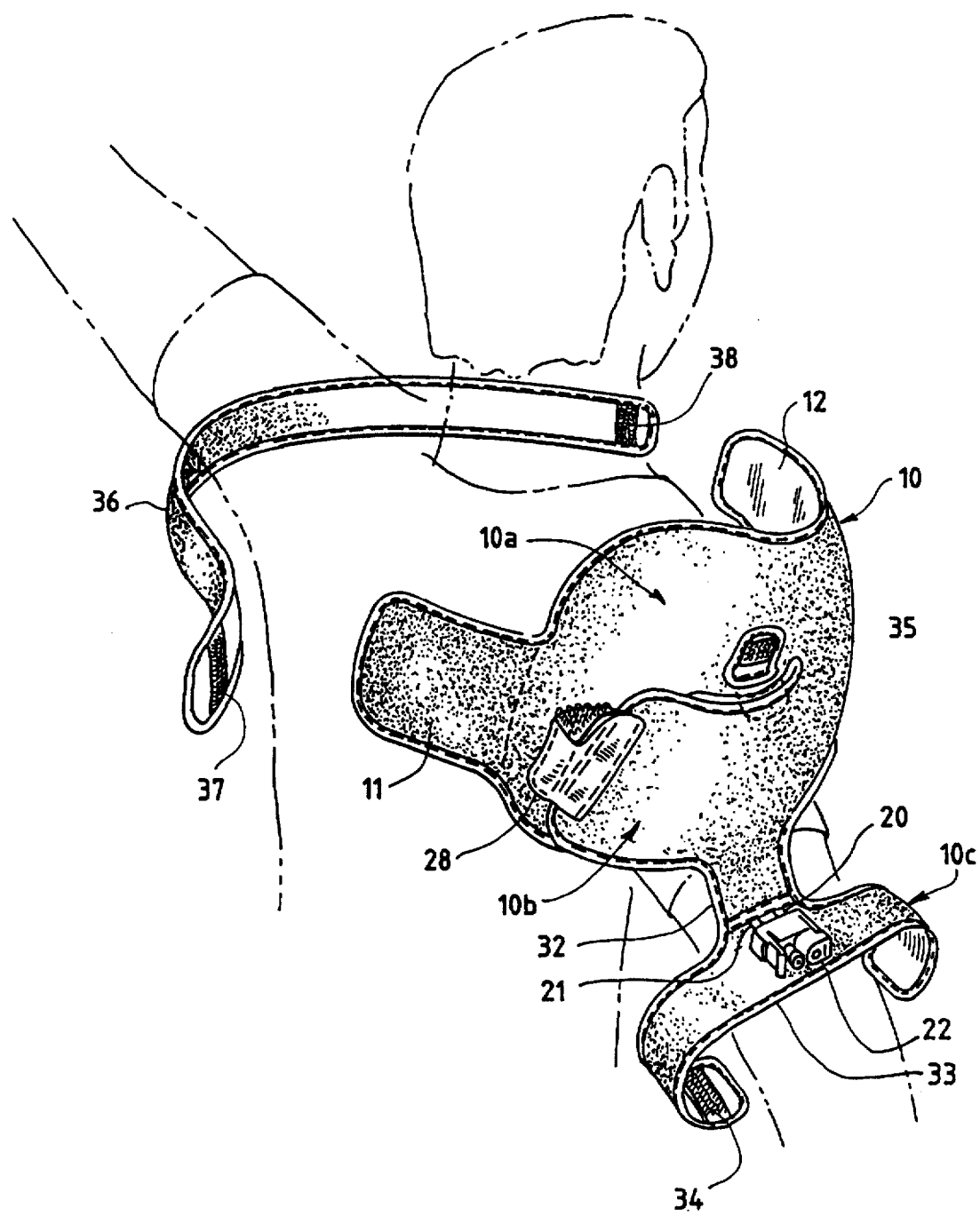
FIG. 8 is a perspective view depicting how the same blanket would be fitted over a patient's right shoulder.

Referring to the drawings, the numeral 10 generally designates a fluid-circulating thermal blanket for post-operative treatment of a joint area of the body. The particular blanket shown in the drawings is designed specifically for the post-operative treatment of the shoulder area; however, many of the important features described hereinafter are also suitable for use on blankets shaped to be wrapped over or about other joint areas such as the knee, elbow, and ankle joints.

The shoulder blanket may be laid flat and is manufactured in planar condition, a feature most advantageous from the standpoint of manufacturing efficiency and purchaser cost. The blanket's outline is of distinctive and irregular shape and generally defines two main sections 10a and 10b arranged in a generally C-shaped configuration, a T-shaped limb-wrapping section 10c, and a pair of integral flap portions 11 and 12 which project outwardly from the first main section 10a.

The blanket is generally composed of two panels: a bodyside or inner panel 13 and an exterior or outer panel 14. As shown most clearly in FIG. 4, the bodyside panel is composed of double layers 13a and 13b of thin, flexible thermoplastic sheet material joined together along heat seal zones 15 to define at least one, and preferably two, serpentine fluid flow passages 16 and 17 leading from a single inlet 18 to a single outlet 19 (FIG. 2). Flexible inlet and outlet tubes 20 and 21 are sealed to and communicate with inlet 18 and outlet 19, respectively, and the opposite ends of the tubes are joined to a fluid coupling element 22 for operatively connecting the blanket to the equipment 23 that circulates the water or other thermal fluid and cools (or heats) that fluid to a selected temperature for circulation through the passages of the blanket. Most advantageously, the coupling element 22 is of the self-sealing, quick-disconnect hermaphroditic type as disclosed in detail in co-owned U.S. Pat. Nos. 4,982,736 and 4,951,665, the disclosures of which are incorporated by reference herein. A flow restrictor in the form of a tubular insert 24 having a reduced flow passage is located in outlet tube 21 (or in the adjacent fitting of coupling element 22) for back-pressuring the passages of the blanket for maintaining them in fluid-filled condition during use.

Referring to FIGS. 2 and 3, it will be observed that the serpentine passages 16 and 17 extend in approximately the same directions through substantially the entire area of bodyside panel 13 but each such passage has a separate zigzag configuration that promotes thermal transfer and, at the same time, reduces the possibility that folding of the blanket in normal use might result in kinking and flow obstruction. For example, referring to FIG. 3, passage 17 extends back and forth in a pattern characterized by relatively long tubular leg portions 17a alternately extending in reverse directions and connected by relatively short tubular connecting portions 17b. The same observation applies to the relatively long tubular leg portions 16a and relatively short tubular connecting portions 16b of adjacent flow passage 16. The pattern is a developed one with the relatively long tubular portions 16a and 17a extending in the direction of expected folding of that portion of the blanket through which they pass, and with the relatively short tubular connecting portions 16b and 17b generally traversing the directions of such folds. The result is that normal folding of the blanket is unlikely to result in obstruction of either passage 16, 17 because the folding action tends to be accommodated by a slight torsional or twisting action of the longer tubular leg portions 16a and 17a and the folding of a blanket in normal use is not abrupt enough to result in kinking of the relatively short connecting portions 16b and 17b, partly because of their small size in relation to the radius of the fold and partly because their reduced dimensions coupled with their compound curves provides them with increased stiffness and resistance to kinking. However, if localized forces should somehow be applied to one of the passages 16 or 17 while the blanket is in use, the companion passage may still circulate thermal fluid throughout the blanket and thereby avoid interruption of thermal treatment.

Exterior panel 14 of the blanket has an outline similar to that of bodyside panel 13 with the edges of the two panels secured together by stitching 25 or by other suitable attachment means. The exterior panel is formed of soft, insulating, easily-foldable fabric or other suitable sheet material. Of particular importance is the fact that its entire outer surface is composed of a loop-providing pile capable of releasably interlocking with VELCRO® nylon hook-providing patches. The fabric of the exterior panel may be multiple-layered as indicated in FIGS. 4–6, with one layer 14a being composed of nylon loop-providing fabric and the other layer 14b being of a soft thermally-insulating material such as a closed-cell polyester foam backed by nylon jersey. Effective results have been obtained using a nylon loop fabric with polyester foam core and nylon jersey backing marketed under the "TEMPO" trademark by Lockfast, Cincinnati, Ohio, but other materials having similar properties are commercially available and may be used.

Figure 9:
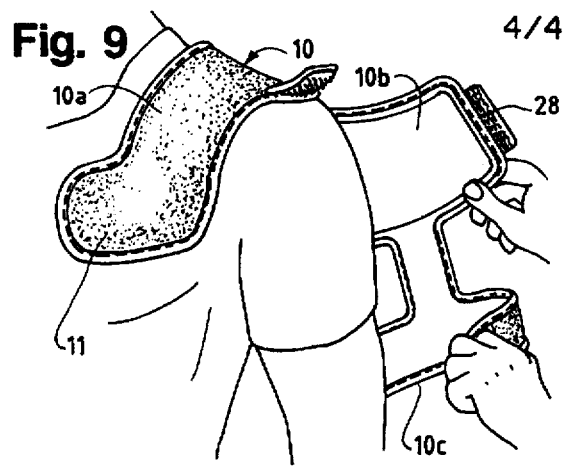
FIGS. 9–14 are perspective views illustrating the sequence of steps in fitting the shoulder blanket upon a patient.
Figure 10:
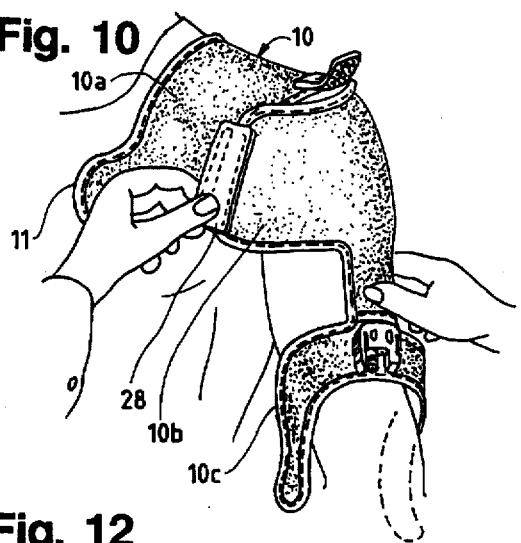

The first and second sections 10a and 10b of blanket 10 are arranged in a generally C-shaped configuration with the second section terminating in a substantially straight edge 26 at its free end 27. An attachment patch 28 is secured to the free end 27 by stitching 29 or by any other suitable means and, as shown clearly in FIGS. 1 and 2, projects well beyond edge 26. The rectangular patch is ideally formed of stretchable elastic fabric with directions of stretch and recovery extending at right angles to edge 26. Along its bodyside surface, the attachment patch is provided with a strip 30 of hook-providing fabric 31. The hooks of the VELCRO® fabric interlock with the loop pile of the first section 10a when the patch 28 and end portion 27 are brought into overlapping relation with the first section in the manner depicted in FIGS. 7, 8, and 10. Since almost the entire exterior surface of the blanket is formed of such loop pile fabric, it is believed that a wide range of adjustment is possible simply by varying the extent of overlap to bring the blanket into snug fitting relation over and about a patient's shoulder. When the blanket is properly fitted, section 10a extends over the top of the shoulder and section 10b wraps about the side of the shoulder (FIGS. 9, 10).

The same blanket may be fitted onto either the right or left shoulder. As shown in FIGS. 7 and 8, when the blanket is fitted upon a patient's left shoulder, attachment patch 28 overlaps the blanket's first section 10a at the front or chest of the patient, whereas if the blanket is fitted onto the patient's right shoulder, the overlap occurs over the patient's back.

The elasticity of the fabric patch 28 helps insure a snug fit of the blanket about a patient's shoulder, with the patch preferably being in a slightly stretched condition to maintain the blanket under a state of tension. The stretchability of the patch accommodates limited movement of the joint and also reduces the possibility that sudden or extreme movement might result in unintentional detachment of the hook-providing patch from the loop pile surface of the blanket.

Limb-attachment section 10c is generally T-shaped in configuration, having a central strap portion 32 extending from the second section 10b of the blanket and terminating in an elongated band portion 33 extending at right angles to the strap portion. The T-shaped section 10c is preferably formed of double thicknesses of the same loop pile fabric as the outer panel 14 of the remainder of the blanket. Inlet and outlet tubes 20 and 21 extend through the strap portion and terminate at the band portion where they join with coupling element 22. As shown in FIGS. 1, 7 and 8, the tubes 20, 21 exit from the strap portion at band portion 33 with coupling element 22 being located on the outside or exterior surface of the band portion. The fluid coupling element is therefore readily accessible for coupling to a mating element and, at the same time, the band portion prevents direct contact between element 22 and a wearer's arm.

Figure 13:
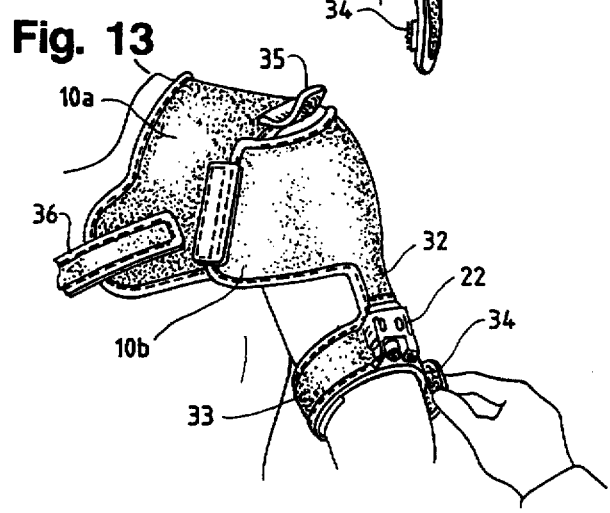

At one of its ends, the band portion 33 is provided along its inside surface with a hook-providing fabric attachment patch 34. In use of the blanket, the band portion is wrapped about the patient's upper arm with patch 34 being brought into contact with the soft, loop pile outer surface of the band's other end portion to secure the fluid coupling element 22 in the position shown. (FIG. 13). Movement of the coupling element and twisting and possible kinking of tubes 20 and 21 are thereby effectively prevented.

One of the main sections of the blanket, section 10a in the embodiment illustrated, may be provided with a VELCRO® tab or flap 35 for engaging the loop pile surface of the other main section 10b along the corner of the patient's shoulder, thereby closing the small gap that might otherwise exist between the edges of sections 10a and 10b when the blanket is in place.

The flaps 11 and 12 which extend from blanket section 10a provide attachment areas for the ends of a body strap 36 that extends about the patient's upper torso beneath the arm opposite from the shoulder undergoing treatment. The body strap 36, shown most clearly in FIGS. 7 and 8, may be composed of double thicknesses of the same loop pile fabric-used for the exterior layers of blanket sections 10a and 10b. Hook-providing VELCRO patches 37 and 38 are located at the ends of the body strap for engagement with soft pile outer surfaces of flaps 11 and 12 when the blanket is worn.

It has been found useful to interpose soft, resilient foam pads or cushions at certain locations between the inner and outer panels of the blanket to insure that the passage-providing panel of the blanket will be maintained in good thermal exchange relation with areas of the shoulder where slight depressions commonly exist. Two such resilient foam pads 39 and 40 are provided between the panels of blanket section 10a as shown in FIGS. 2 and 6. If desired, a resilient foam strip may also be interposed between the double thicknesses of the body strap 36.

Figure 11:
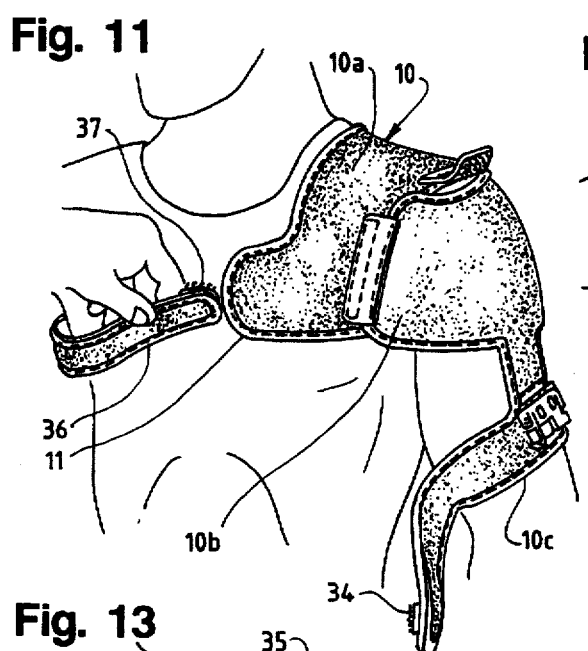
Figure 12:
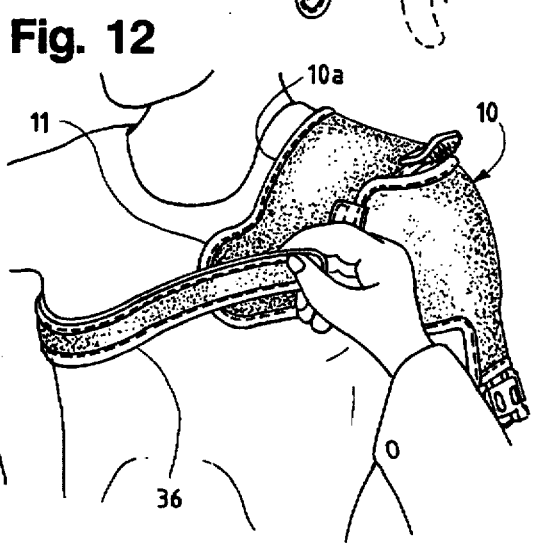
Figure 14:
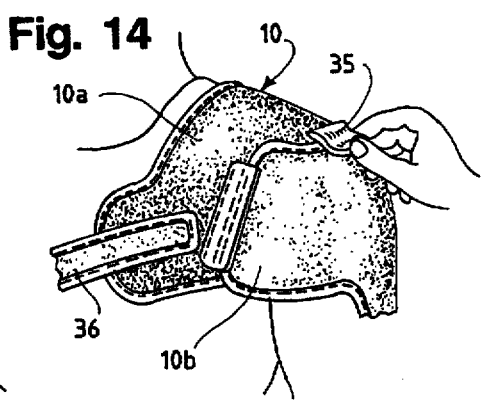

FIGS. 9–14 illustrate the sequence of steps in fitting the blanket about a patient's left shoulder. Blanket section 10a is extended over the top of the shoulder (FIG. 9) and section 10b is wrapped about the side of the shoulder and secured in place by means of stretchable attachment patch 28 (FIG. 10). Body strap 36 is then extended about the patient's body beneath his/her opposite arm and its opposite ends are secured to the flaps 11, 12 overlying the patient's chest and back (FIGS. 11, 12). The limb band portion 33 of the T-shaped section 10c is wrapped and fastened about the patient's upper arm (FIG. 13), and the VELCRO® flap or tab 35 is fixed in position to secure the edges-of blanket sections 10a and 10b together and close any gap that might otherwise exist between those edges (FIG. 14).

While in the foregoing, an embodiment of the invention has been disclosed in considerable detail for purposes of illustration, it will be understood by those skilled in the art that many of these details may be varied without departing from the spirit and scope of the invention.

I claim:

1. A thermal blanket for post-operative treatment of joint areas of the body, comprising a foldable bodyside panel composed of double layers of thermoplastic sheet material heat-sealed together to define therebetween two spaced apart serpentine fluid-flow passages extending substantially throughout the entire area of the bodyside panel from an inlet opening to an adjacent outlet opening and with each passage following a separate unbranched zigzag pathway; each of said flow passages communicating at one end thereof with said inlet opening and at the other end thereof with said outlet opening; and a soft, foldable exterior panel extending along said bodyside panel in parallel relation therewith; said bodyside and exterior panels being coplanar and having peripheral edges secured together to form a unitary foldable blanket with an outline defining a pair of main blanket sections; said exterior panel having a soft loop-providing pile over substantially the entire exterior surface thereof; one of said main blanket sections being provided with an attachment patch having a bodyside-facing hook-providing fabric for releasable attachment to said loop-providing pile of said exterior surface of the exterior panel for maintaining said sections in partially overlapping interlocked relation when said blanket is wrapped about a joint area for thermal treatment thereof; said attachment patch projecting beyond a free edge of said one section and being elastically stretchable and contractable in directions towards and away from said free edge.

2. The blanket of claim 1 in which said blanket includes an integral T-shaped section having a central strap portion and an elongated transversely-extending limb-wrapping band portion; said T-shaped section having a soft loop-providing pile over substantially the entire exterior surface thereof; said band portion having a hook-providing bodyside-facing attachment patch at one end thereof for releasable attachment to the loop-providing pile of said band portion when the same is wrapped about a limb in close proximity to said joint area.

3. The blanket of claim 1 in which each said serpentine flow passage extending along said zigzag pathway includes relatively long tubular portions extending generally parallel with the directions of folding of the blanket in use, with such relatively long tubular portions being connected by and communicating with relatively short tubular portions traversing such directions of folding.

* * * * *